United States Patent [19]
Beversdorf et al.

[11] Patent Number: 5,628,145
[45] Date of Patent: May 13, 1997

[54] PROCESS FOR PRODUCING SEEDS CAPABLE OF FORMING $F_1$ HYBRID PLANTS UTILIZING SELF-INCOMPATIBILITY

[75] Inventors: Wallace D. Beversdorf, Greensboro, N.C.; Laima S. Kott, Guelph, Canada; Van L. Ripley, Saskatoon, Canada; Jeff P. Parker, Calgary, Canada; Paul R. Banks, Guelph, Canada

[73] Assignee: University of Guelph, Guelph, Canada

[21] Appl. No.: 383,566

[22] Filed: Feb. 3, 1995

[51] Int. Cl.$^6$ ................................ A01H 1/00; A01H 3/00
[52] U.S. Cl. .................... 47/58; 47/DIG. 1; 800/200; 435/172.1
[58] Field of Search .................... 800/200, 205, 800/230, 250; 47/58; 435/172.1, 2

[56] References Cited

U.S. PATENT DOCUMENTS 5,043,282  8/1991  Scott-Pearse ..................... 435/240.49

OTHER PUBLICATIONS

Poehiman "Breeding Field Crops" AVI Publishing Co., INC. WestPort Connecticut, pp. 132–134, 228–229 and 428. 1987.
"Methods of Breeding: Cross Pollinated Crops, Asexually Propagated Crops", J.M. Poehlman, *Breeding of Field Crops*, pp. 133 to 140 (1979).
"Self–Incompatibility and Rapeseed Breeding", Ph.D. dissertation of Paul Banks, The University of Guelph (1988).
"Genetic Studies on Self–Incompatibility as a Pollination Control System in Oilseed Rape"(*Brassica napus* L. ssp. *oleifera*), Ph.D. dissertation of J.P. Parker, The University of Guelph (1994).
"Non–linear Dominance Relationships Between S Alleles", K.F. Thompson and J.P. Taylor, *Heredity*, Vol. 21, pp. 345–362 (1966).
"Production of Hybrid Seed Using Male Sterility or Self–Incompatibility", Q.P. Van der Meer and M. Nieuwhof, *Euphytica*, Vol. 17, pp. 284–288 (1968).
"Single and Double Crosses of Cole Crops (*Brassica oleracea*L.)", M. Nieuwhof, Proceedings of the Brassica meeting of Eucarpia, Inited Kingdom, pp. 2 to 4 (1968).
"Selection for High Self–Incompatibility in Inbred Lines of Brussel Sprouts", D.J. Ockendon, *Euphytica*, Vol. 22, pp. 503 to 509 (1973).
"Dominance Relationships Between S–Alleles in the Stigmas of Brussels Sprouts (*Brassic oleracea* var. *Gemmifera*)", D.J. Ockendon, *Euphytica*, Vol. 24, pp. 165 to 172 (1975).
"Methods of Producing $F^1$ Hybrid Swedes (*Bassica napus* ssp. *rapifera*)", S. Gowers, *Euphytica*, Vol. 24, pp. 537 and 541 (1975).
"Breeding Structure of a Highly Selected Cultivar of Cabbage (*Brassica oleracea* var. *Capitata*)", D.J. Ockendon and L. Currah, *Heredity*, Vol. 43, pp. 373 to 379 (1979).
"Breeding Hybrid Varieties of Rape", Gerhard Röbbelen, from Hybrid Seed Production of Selected Cereals, Oil & Vegetable Crops, FAO, Rome, pp. 133 to 147 (1987).
"Self–incompatibility interactions in *Brassica napus*", S. Gowers, *Euphytica*, Vol. 42, pp. 99 to 103 (1989).
"Self–incompatibility as a Pollination Control Mechanism for Spring Oilseed Rape, *Brassica napus* L.", P.R. Banks and W.D. Beversdorf, *Euphytica*, Vol. 75, pp. 27 to 30 (1994).

*Primary Examiner*—Gary Benzion
*Attorney, Agent, or Firm*—Burns, Doane, Swecker & Mathis

[57] ABSTRACT

An improved route is provided for the production of seeds capable of forming $F_1$ hybrid plants of a crop which is capable of undergoing cross-pollination while utilizing self-incompatibility. A substantially randomly mixed population of parent plants is utilized that are substantially incapable of undergoing self-pollination under conventional growing conditions wherein the inability to undergo self-pollination is attributable in each of the parent plants to at least one heterozygous dominant genetic determinant for sporophytic self-incompatibility that is different in each parent. All plants are capable of serving (1) as seed parents which following cross-pollination with pollen from the other parent plants bear seeds capable of forming $F_1$ hybrid plants of a predetermined cultivar, and (2) as pollen parents for other parent plants. The non-selective simultaneous harvest by conventional means from both parent plants of seed capable of forming a single predetermined cultivar of $F_1$ hybrid plant is made possible. The resulting product exhibits heterosis that makes possible increased yields for the grower. In a particularly preferred embodiment the crop is canola-quality *Brassica napus*.

13 Claims, No Drawings

PROCESS FOR PRODUCING SEEDS CAPABLE OF FORMING $F_1$ HYBRID PLANTS UTILIZING SELF-INCOMPATIBILITY

BACKGROUND OF THE INVENTION

It long has been recognized that the hybridization of plants from differing genetic backgrounds commonly leads to the production of $F_1$ hybrid plants in the first filial generation that possess an increased vigor or heterosis. Such condition is being widely utilized to make possible greater yields in a number of economically significant crops.

Since the parent plants utilized in the hybridization cross commonly are capable of undergoing both self-pollination and cross-pollination, a reliable means must be provided to ensure the consistent formation and harvest of seeds that upon growth will manifest the desired hybrid vigor. Techniques available to achieve this objective have included the mechanical emasculation of seed parent plants, the utilization of gametocides, the utilization of cytoplasmic male sterility, the utilization of male sterility that is controlled solely by nuclear genes, and self-incompatibility of the sporophytic or gametic types. Also, herbicide tolerance sometimes has been imparted to the seed parent plants so that the pollen parent plants used in the cross-pollination can be destroyed at the appropriate time through the use of a herbicide.

To date self-incompatibility has been utilized in some limited areas for the production of $F_1$ hybrid plants. For instance, self-incompatibility commonly has been utilized in the past in the hybrid production of vegetable Brassica oleracea plants, such as cabbage, broccoli, Brussels sprouts, and cauliflower. See, also U.S. Pat. No. 5,043,282 entitled "Method of Producing Plant Cell Lines of Plant Hybrids" to Frank Scott-Pearse. In the previously proposed hybridization technology utilizing self-incompatibility, it has been the consistent practice to grow adjoining uniform population of each of the parent plants followed by the selective harvest of the $F_1$ hybrid seeds that are formed on the seed parent plants. Such selective planting and selective harvest procedures are time consuming and tedious to implement on a reliable basis and further add significantly to the production costs in view of the fact that the $F_1$ hybrid seeds are formed on only a portion of the planting area. The possibility for error at each step is great and in those instances where an error occurs, the consequences tend to be drastic for the consumer. See, for instance, (1) "Breeding Field Crops" by J. M. Poehlman at Pages 132 to 134, Van Nostrand Reinhold Co. Inc., N.Y. (1987); (2) the Ph.D. dissertation of P. Banks of the University of Guelph, Guelph, Ontario, Canada, entitled "Self-Incompatibility and Rapeseed Breeding" (1988); and (3) the Ph.D. dissertation of J. P. Parker of the University of Guelph, Guelph, Ontario, Canada, entitled "Genetic Studies on Self-Incompatibility as a Pollination Control System in Oilseed Rape (Brassica napus L. ssp. oleifera)" (1994).

Numerous alleles for self-incompatibility in a number of crops have been identified in the past and are already known and available to plant scientists. Others can be located in available source materials using recognized screening techniques of a routine nature that can be carried out without undue experimentation.

It is an object of the present invention to provide an improved hybridization process for the production of a predetermined $F_1$ hybrid cultivar.

It is an object of the present invention to provide an improved hybridization process for the production of a predetermined $F_1$ hybrid cultivar that utilizes self-incompatibility as the pollination control mechanism.

It is an object of the present invention to provide an improved hybridization process for the production of a predetermined $F_I$ hybrid cultivar wherein each parent plant is randomly grown in the same planting area, and the resulting harvest is non-selective with respect to each of the parent plants.

It is an object of the present invention to provide an improved hybridization process for the production of a predetermined $F_1$ hybrid cultivar that is readily amenable for commercial implementation on an economical basis.

It is an object of the present invention to provide an improved hybridization process for the production of a predetermined $F_1$ plant cultivar wherein the necessary pollination control is readily maintainable.

It is an object of the present invention to provide an improved hybridization process that utilizes self-incompatibility wherein the requisite foundation seed required for the formation of the parent plants can be produced under field growing conditions.

It is an object of the present invention to provide an improved hybridization process that in particularly preferred embodiments is suitable for the production of a predetermined $F_1$ hybrid cultivar of Brassica napus or Brassica campestris (syn. Brassica rapa L.).

It is another object of the present invention to provide a blend (i.e., a mixture) of seeds that is useful during $F_1$ hybrid seed production in accordance with the concept of the present invention.

It is a further object of the present invention to provide a field of plants that is useful for $F_1$ hybrid seed production in accordance with the concept of the present invention.

These and other objects, as well as the scope, nature, and utilization of the claimed invention will be apparent to those skilled in plant science from the following detailed description and appended claims.

SUMMARY OF THE INVENTION

It has been found that an improved process for producing seeds capable of forming predetermined $F_1$ hybrid plants of a crop which is capable of undergoing cross-pollination comprises:

(a) growing in a planting area a substantially randomly mixed population of parent plants that are substantially incapable of undergoing self-pollination under conventional growing conditions wherein the inability to undergo self-pollination is attributable in each parent to at least one heterozygous dominant genetic determinant for sporophytic self-incompatibility that is different in each parent wherein substantially all plants of the crop present in the planting area are capable of serving (a) as seed parents which following cross-pollination with pollen from the other parent plants bear seeds capable of forming $F_1$ hybrid plants of a predetermined cultivar and (2) as pollen parents for other parent plants growing in the planting area, (b) cross-pollinating the plants growing in the planting area with pollen derived from the other parent plants growing in the planting area and forming seeds capable of producing a predetermined cultivar of $F_1$ hybrid plants on substantially all plants growing in the planting area as a result of the cross-pollination, and (c) harvesting in bulk the seeds that are capable of forming a predetermined cultivar of $F_1$ hybrid plants that form on both parent plants of the planting area.

A blend of seeds of a crop that is capable of undergoing cross-pollination is provided wherein the seeds are useful during $F_1$ hybrid seed production and are capable of forming parent plants that are substantially incapable of undergoing self-pollination under conventional growing conditions wherein the inability to undergo self-pollination is attributable in each of the parent plants to at least one heterozygous dominant genetic determinant for sporophytic self-compatibility that is different in each parent wherein substantially all of the resulting plants are capable of serving (1) as seed parents which following cross-pollination with pollen from the other parent plants bear seeds capable of forming $F_1$ hybrid plants of a predetermined cultivar and (2) as pollen parents to pollinate the plants of the other parent.

A field of plants of a crop that is capable of undergoing cross-pollination is provided wherein the plants are useful for $F_1$ hybrid seed production and consist of a substantially randomly distributed population of parent plants that are substantially incapable of undergoing self-pollination under conventional growing conditions wherein the inability to undergo self-pollination is attributable in each of the parent plants to at least one heterozygous dominant genetic determinant for sporophytic self-incompatibility that is different in each parent wherein substantially all plants present in the field are capable of serving (1) as seed parents which following cross-pollination with pollen from the other parent plants bear seeds capable of forming $F_1$ hybrid plants of a predetermined cultivar and (2) as pollen parents to pollinate the plants of the other parent.

DETAILED DESCRIPTION

The hybridization process of the present invention is generally applicable for practice with any crop that is capable of undergoing cross-pollination and possesses genetic determinants for the requisite self-incompatibility. For the purposes of the present invention hybridization is deemed to occur when two parent plants of differing genotypes are cross-pollinated. For the exhibition of maximum heterosis the parents commonly are selected from inbred populations with significantly different but complementary genetic backgrounds so as to possess a high general and specific combining ability.

Representative crop types with the required genetic determinants for sporophytic incompatibility for hybridization in accordance with the concept of the present invention include cereals (e.g., rye), and oilseeds (e.g., mustard, rape, etc.). Additional plants can be utilized that can be rendered self-incompatible yet cross-compatible with respect to pollination through introgression or transgenic insertion of appropriate genetic determinants that when phenotypically expressed, functionally mimic the prerequisites of the present invention.

The process of the present invention is particularly suited for the formation of a $F_1$ hybrid cultivar of a crop of the family Brassicaceae, which is sometimes designated the Cruciferae family or the Mustard family. Within this family one may select with greater particularity a crop of the genus Brassica (e.g., a hybrid cultivar of rape plant classified as *Brassica napus* or *Brassica campestris*). The *campestris* species is sometimes identified as the *rapa* species. Each of these species occurs in a spring and a winter (fall-seed) type. High-quality forms of rapeseed which are used primarily as a source of vegetable oil and of rapeseed meal (a protein concentrate for livestock) are commonly referred to as canola. For instance, canola often identifies quality rapeseed which is low in erucic acid in the vegetable oil (e.g., less than 0.1 percent by weight, and preferably less than 0.05 percent by weight) and low in glucosinolates in the oil-free meal (e.g., less than 30 micromoles per gram). Alternatively, the rapeseed product can be employed in the production of lubricants, paints, varnishes, and plastics in accordance with known technology.

When carrying out the process of the present invention, parent plants are selected that are substantially incapable of undergoing self-pollination under conventional growing conditions wherein the inability to undergo self-pollination is attributable to at least one heterozygous dominant determinant for sporophytic self-incompatibility that is different in each parent. This means that pollen produced on a given plant will not pollinate that plant or other plants possessing the same allele or alleles for self-incompatibility under normal growing conditions. The parent plants may be individually selected from an inbred population so as to be an inbred line but for the heterozygous dominant determinant for self-incompatibility, or be the product of a cross of parents having more diverse genetic backgrounds, etc. The different determinants for self-incompatibility in each parent plant are selected so as to be capable of independent expression. Also, such determinants are dominant in nature in that the self-incompatibility is reliably expressed even though it is provided in the heterozygous state in each parent plant. In some instances, the determinant for self-incompatibility corresponds to a single allele. The determinants for self-incompatibility may be located at different loci within each of the parent plants or at the same locus or loci with different alleles being operative in each instance. The self-incompatibility in each parent plant is sporophytic in the sense that the incompatibility is imparted to the pollen by the plant upon which the pollen is borne. Such incompatibility already is known and discussed in the literature and may result from incompatibility between pollen or pollen tubes and stigmatic or stylar tissues of plants that phenotypically express the same genetic incompatibility determinant. In some instances the barrier to self-fertilization can be traced to the cuticle on the stigma wherein an incompatibility substance in the stigma commonly activates a cutinase enzyme in the pollen from another cross-compatible plant, but inhibits this enzyme system in pollen that possesses the same allele for sterility. In any event the pollen does not readily germinate and fertilize if it falls on its own flowers or on flowers of other plants carrying the same allele. However, the stigma and style of the self-incompatible plant generally is receptive and supportive to pollen and the pollen tube from a plant that does not contain the same self-incompatibility determinant. This ensures adequate cross compatibility during $F_1$ hybrid seed production.

Numerous dominant allelic determinants for sporophytic self-incompatibility are known and are available in *Brassica oleracea* where they occur naturally and are routinely being utilized in the production of vegetable crops, such as cabbage, broccoli, and Brussels sprouts. Other dominant allelic determinants for sporophytic self-incompatibility are known and available in *Brassica campestris* and *Brassica napus* ssp. *rapifera*. The determinants for self-incompatibility originating in other species can be transferred to *Brassica campestris* and/or *Brassica napus* (sometimes known as Argentine rape or swede rape) by interspecific introgression followed by recurrent selection using standard backcrossing and with or without embryo rescue techniques that are known and practiced by plant scientists. When a cross between *Brassica oleracea* and *Brassica napus* is made, the use of embryo rescue for the first two cycles may be helpful to overcome chromosomal aberrations that otherwise could interfere with embryo development. A transfer of the desired self-incompatibility determinant readily can be carried out between *Brassica campestris* and *Brassica napus*. Since *Brassica napus* possesses 38 chromosomes and is an allotetraploid of the genomes of *Brassica oleracea* that possesses 18 chromosomes and of *Brassica campestris* that possesses 20 chromosomes, this transfer tends to be straightforward. In such instances, the resulting *Brassica napus* plant following introgression can in a preferred embodiment contain a determinant for sporophytic self-incompatibility derived from *Brassica oleracea* and another determinant for sporophytic self-incompatibility derived from *Brassica campestris* with each determinant thereby being present at a different locus. In the course of such introgression, selections concomitantly are made in order to eliminate undesirably high erucic acid and/or gluconsinolate levels that commonly are exhibited in source materials such as *Brassica oleracea*. Resynthesis of *Brassica napus* can be accomplished by interspecific hybridization and chromosome doubling or protoplast fusion, if desired wherein *Brassica campestris* and *Brassica oleracea* are joined.

It has been found that the Candle and Tobin cultivars of *Brassica campestris* can be looked to as representative preferred sources for dominant genetic determinants for self-incompatibility that can be utilized in the improved hybridization process of the present invention. Such cultivars are known and are publicly available from a number of sources that are accessible by those working in the area of rapeseed technology. Representative dominant alleles for sporophytic self-incompatibility from the Candle cultivar designated 1, 4, and 5, have already been discussed in the literature. It has been found that numerous additional alleles for self-incompatibility can be isolated from the Candle cultivar while using cyclic inbreeding as indicated hereafter. Additional representative preferred alleles for sporophytic self-incompatibility have been derived from the Tobin cultivar as indicated hereafter. Other preferred sources for alleles for self-incompatibility for sporophytic use in the present invention are *Brassica napus* ssp. *rapifera*, and *Brassica oleracea* ssp. *italica*. For instance, the 2 sporophytic self-incompatibility allele previously has been reported as being present in *Brassica napus* ssp. *rapifera*, and the s2 and s13 self-incompatibility alleles previously have been reported as being present in *Brassica oleracea* ssp. *italica*. Additional dominant self-incompatibility alleles that can be similarly isolated by those or ordinary skill in rapeseed technology from these and other publicly available sources via cyclic inbreeding. It has been found through empirical research, that literally dozens of different dominant genetic determinants for sporophytic self-incompatibility suitable for use in the improved process of the present invention are available in existing and publicly available rape germplasm sources where the requisite self-incompatibility is known to be operative and can be located through the use of known screening techniques. Whenever possible in preferred embodiments, the necessary alleles for sporophytic self-incompatibility should be located in synthetics or registered cultivars of rapeseed of canola quality so as to minimize the plant breeding efforts required to provide parent plants that concomitantly exhibit satisfactory or superior agronomic characteristics.

In preferred embodiments, more than one heterozygous dominant genetic determinant for sporophytic self-incompatibility (e.g., two, three, four, or more) are provided in each of the parent plants so long as the determinants are different in each parent. Such redundancy of dominant genetic determinants can be utilized in order to provide means for exerting a firmer control over the sporophytic self-incompatibility that is operative, and will minimize the possibility of a breakdown of the desired incompatibility should unusual growing or environmental conditions be encountered during the course of $F_1$ hybrid seed production.

Once a suitable plant possessing the requisite sporophytic self-incompatibility is isolated and/or produced via plant breeding or other means, it is maintained and multiplied via self-pollination as breeder or prebasic seed with the at least one dominant determinant for self-incompatibility being present in the homozygous state through one or more generations with the use of means to overcome the sporophytic self-incompatibility while precluding the introduction of unwanted pollen from extraneous sources. Adequate isolation from unwanted pollen sources must be provided as will be apparent to those skilled in plant breeding.

The sporophytic self-incompatibility commonly is inactive in the bud stage and bud pollination accordingly can be employed to overcome such incompatibility. Following surgical exposure the stigmas will accept via hand pollination germinating pollen at this time to accomplish self-pollinated seed set. However, it will be apparent that only small quantities of seed can be formed from a practical standpoint while using the bud pollination procedure.

Alternatively, the sporophytic self-incompatibility can be overcome by subjecting the plants to increased levels of carbon dioxide (e.g., approximately 2 to 20 percent by volume for approximately 2 to 24 hours) during the flowering period whereby the plant's own pollen can be caused to accomplish germination and to grow on the stigma. The increased carbon dioxide environment serves to alter the cuticular surface of the stigma enough to enable the pollen tube penetration of germinating pollen grains that would otherwise be incompatible with the stigma tissue. In a preferred embodiment the carbon dioxide is provided at a concentration of approximately 8 to 12 percent by volume for approximately 3 to 4 hours. Although the procedure can be repeated daily or be carried out only once during the flowering period, the increased carbon dioxide environment optimally is provided every 2 to 3 days during the flowering period. The use of carbon dioxide to overcome sporophytic self-incompatibility can be carried out indoors or outdoors. For instance, when operating indoors plants can be individually bagged with gas-permeable bags while present in an enclosed chamber and shaken by hand to aid in the dispersal of the pollen. When operating outdoors, plants can be temporarily covered with a gas impervious barrier (e.g., polyethylene film stretched over hoops) at the onset of flowering. Carbon dioxide is then introduced at appropriate intervals with the pollination being further enhanced by releasing pollinating-insects (e.g., bees) inside the enclosure.

In a further embodiment, chemicals, such as a dilute aqueous solution of sodium chloride, can be applied to the surface of the stigmas at the flowering time to make possible pollen tube penetration. The salt application can be carried out daily or at intervals throughout the flowering period with the salt concentration in an aqueous solution commonly ranging from approximately 1 to 10 w/v percent. Backpack sprayers or tractor spray attachments can be utilized. Since the salt may have a detrimental influence on the overall well being of the plants, such treatment preferably should be kept to the minimum required to accomplish the desired result. For instance, commonly one can apply a fine spray of a 4 w/v percent aqueous sodium chloride solution every three days during the flowering period for optimum seed set while experiencing minimal harm to the plant in other areas. If desired, a dilute sodium chloride solution can be selectively applied to the plant stigmas with a small cotton swab and the pollen also can be transferred by hand using the same swab. While using this technique pollen has been found to survive contact with the sodium chloride solution and the overall health of the plant is better maintained since the sodium chloride solution comes in contact with only the stigmatic regions. Inbred lines can be produced while overcoming the sporophytic self-incompatibility as described by self-pollination over several generations (e.g., 4 or 5 generations) or until no more segregation of alleles for self-incompatibility is observed. Sibbing involving the crossing of progeny from self-pollinated seed can be used to identify individuals having the same alleles for self-incompatibility. Also, immediate homozygosity can be obtained through doubled haploid production in accordance with known techniques. See additionally U.S. Pat. No. 5,043,282 identified earlier.

The maintenance and multiplication of the breeder or prebasic seed wherein the at least one dominant determinant for sporophytic self-incompatibility is in the homozygous state by necessity is somewhat tedious and exacting in nature and tends to be somewhat difficult to implement on a large scale. Accordingly, in accordance with the concept of the present invention, such seed is next multiplied more expeditiously during the formation of foundation or basic seed wherein each dominant determinant for sporophytic self-incompatibility that is present in the homozygous state in the breeder or prebasic seed is converted to the heterozygous state. This can be accomplished by growing with care plants formed from the breeder or prebasic seed as a substantially homogenous population in pollinating proximity to a substantially homozygous population of another plant that lacks the same determinant for sporophytic self-incompatibility followed by the selective harvest of the resulting seeds that form on the plants resulting from the germination of the breeder or the prebasic seed. Preferred planting patterns during such foundation or basic seed production utilize spatially separated strips. The plants that lack the same determinant for sporophytic self-incompatibility can be an isoline of the breeder or prebasic seed or can be of a dissimilar genetic background. Alternatively, isolines or dissimilar lines each possessing at least one different sporophytic dominant determinant for self-incompatibility in the homozygous state can be grown as a substantially randomly mixed population in the same block and the resulting seed formed thereon harvested in bulk. In the harvested seed, multiple independently operable determinants for self-incompatibility now will be provided with each being present in the heterozygous state. As will be apparent to those skilled in plant breeding, the planting area used for such foundation or basic seed production must be well isolated and removed from extraneous pollen sources in order to retain the necessary genetic control. The production of large quantities of foundation or basic seed is made possible under field growing conditions on an economically feasible basis wherein the dominant determinants for sporophytic self-incompatibility are provided in the heterozygous state in each parent plant.

Seeds capable of forming a predetermined cultivar of $F_1$ hybrid plants is formed by growing in a planting area a substantially randomly mixed population of parent plants that are substantially incapable of undergoing self-pollination under conventional growing conditions wherein the self-incompatibility is attributable in the parent plants to a different heterozygous dominant determinant for sporophytic self-incompatibility. Single, double, triple and four-way crosses are made possible depending upon the backgrounds of each of the parent plants. Standard planting patterns for each crop conveniently can be utilized; however, in some instances special provision must be made for the differing flowering times commonly exhibited by each of the parent plants. For instance, when the parent plants typically flower at substantially the same time at a given planting area, the parent plants can be produced following the simultaneous planting of each parent in the planting area from a single seed blend. If the flowering times of the parent plants commonly differ, the planting of seeds to produce the parent that normally flowers first can be delayed and planted on a later date so as to accommodate the inherent differences in flowering characteristics. Alternatively, if one or more of the parental components of the substantially randomly mixed population initiates flowering earlier than other components of the population, the mechanical clipping of the entire field at a height that severs the inflorescence of the early-flowering plants can be used to effect synchronization of flowering by delaying the development of the early-flowering parental components of the randomly mixed population. Under such circumstances both parent plants can be caused to flower at substantially the same time so that the necessary pollen transfer between plants can be accomplished. As will be apparent to those skilled in plant breeding, the planting area used for the production of seed capable of forming $F_1$ hybrid plants must be sufficiently isolated from extraneous pollen sources so as to retain the requisite genetic control that leads to the formation of the predetermined cultivar.

When cross-pollination occurs during the formation of the seeds capable of forming predetermined $F_1$ hybrid plants in accordance with the present invention, substantially all plants present in the planting area serve (1) as seed parents which following cross-pollination with pollen from the other parent plants bear seeds capable of forming $F_1$ hybrid plants of a predetermined cultivar, and (2) as pollen parents for the other plants present in the planting area. The pollen transfer conveniently is carried out by the standard method operative in the subject crop (e.g., by wind and/or the use of pollen-carrying insects, such as bees). The substantially random planting of the parent plants in the planting area ensures that an operative pollen source is always nearby. When one of the parent plants produces viable pollen in more copious quantities than the other, it is possible for the concentration of such parent plant in the randomly mixed population to be correspondingly reduced. Optimum concentrations for each parent plant within the randomly mixed population of the planting area can be determined by routine experimentation taking into consideration the flowering characteristics of the specific parent plants being utilized and the anticipated local environmental conditions that may influence the longevity of the pollen that is formed on the parent plants.

At the appropriate time in the plant life cycle, the seeds derived from the parent plants are harvested in bulk. Such harvesting can be conducted while using standard harvest equipment commonly in use for the subject crop. The resulting seeds are capable of forming a single predetermined $F_1$ hybrid cultivar that following planting is capable for use in the production of a commercial crop. Such seed offers the farmer the ability to grow and to harvest a crop using standard procedures that exhibits beneficial heterosis that is manifest in increased crop yields. While there may be some segregation with respect to self-incompatibility under the control of a specific genetic determinant in the $F_1$ hybrid crop, this is not a problem for the grower since other nearby plants present in the field that lack this characteristic can be relied upon to provide the pollen needed for seed-set. For instance, self-incompatibility among individuals in the hybrid is not a limitation to performance in production, as this is the normal state of conventional synthetic varieties of *Brassica campestris*, rye, and other crops in which the conventional varieties are nearly random mating populations of self-incompatible plants. In *Brassica napus*, mixtures of self-incompatible plants with different incompatibility phenotypes behave as synthetics if pollen availability and mobility are adequate, which are also prerequisites for the production of the foundation (i.e., basic) and $F_1$ hybrid seed.

The following Examples are presented as specific illustrations of the claimed invention. It should be understood, however, that the invention is not limited to the specific details set forth in the Examples.

EXAMPLE I

Plants of the Tobin cultivar of *Brassica campestris* were chosen as a source for dominant genetic determinants for the sporophytic self-incompatibility required to carry out the improved hybridization process of the present invention. Since *Brassica campestris* normally is an obligate outcrossing species, every seed thereof is heterozygotic for the sporophytic self-incompatibility locus. Inbreds of two different dominant alleles for self-incompatibility were isolated by controlled cyclic inbreeding under indoor growing conditions wherein a dilute 4 percent aqueous sodium chloride solution was applied as a fine spray to the stigmas of the recently opened flowers every three days during the flowering period. Such sodium chloride application facilitated pollen tube penetration and self-fertilization of the normally self-incompatible plants. Following such self-pollination the progeny of the plants that were heterozygotic for the sporophytic self-incompatibility at a particular locus segregated with respect the genetically-controlled self-incompatibility characteristic. After several cycles of inbreeding the homozygotes and heterozygotes for self-incompatibility were identified by progeny testing. For instance, when some plants of the S3 seed generation that originated from a single S2 plant when intercrossed showed no further segregation with respect to self-incompatibility, it was determined that the S2 source was homozygous for a dominant genetic determinant for sporophytic self-incompatibility.

Resulting plants that were demonstrated to contain homozygous dominant genetic determinants for sporophytic self-incompatibility were similarly increased under controlled self-pollination conditions using a dilute aqueous sodium chloride solution during the flowering stage to overcome the self-incompatibility that normally was operative.

Rapeseeds of two different *Brassica campestris* inbred lines derived from the Tobin cultivar each containing different homozygous dominant determinants for sporophytic self-incompatibility have been deposited under the Budapest Treaty in the American Type Culture Collection, 12301 Parklawn Drive, Rockville, Md. 20852, U.S.A. One of these deposits has been designated *Brassica campestris* BB and has received Accession No. 75986, and the other has been designated *Brassica campestris* EE and has received Accession No. 75987. Such deposits constitute breeder or prebasic seed that can serve as a source of representative dominant genetic determinants for sporophytic self-incompatibility. When such genetic determinants are converted to the heterozygous state as described herein, they are suitable for use in the improved hybridization process of the present invention.

EXAMPLE II

Plants of the Candle cultivar of *Brassica campestris* were chosen as a source for dominant genetic determinants for the sporophytic self-incompatibility required to carry out the improved hybridization process of the present invention. Cyclic inbreeding as described in connection with Example I was utilized to identify rapeseeds of two different lines from the Candle cultivar containing different homozygous dominant determinants for sporophytic self-incompatibility. Following multiplication as described herein, seeds of these inbred lines have been deposited under the Budapest Treaty in the American Type Culture Collection. One of these deposits has been designated *Brassica campestris* PP and has received Accession No. 75988, and the other has been designated *Brassica campestris* bb and has received Accession No. 75989. When such genetic determinants are converted to the heterozygous state, they are suitable for use in the improved hybridization process of the present invention.

Three additional homozygous dominant determinants for sporophytic self-incompatibility were derived from the Candle cultivar as previously described. These were the same self-incompatibility alleles as identified as 1, 4 and 5 in the Ph.D. dissertations of P. Banks and J. P. Parker of the University of Guelph identified earlier. These determinants were introgressed into plants of the *Brassica napus* species which is an allotetraploid derived from the diploid and self-incompatible species, *Brassica campestris* and *Brassica oleracea* and normally is self-compatible. More specifically, one of these determinants was introgressed into a plant of the Westar cultivar, and the other two determinants were introgressed into different plants of the Hanna cultivar. Plants of the Westar and Hanna cultivars were used as the recurrent parents. Testing for self-incompatibility among the progeny was done by the forced selfing of several open flowers on each plant. Extraction of doubled haploids yielded *Brassica napus* inbreds that were homozygous for all genes including the dominant determinants for self-incompatibility. Following multiplication, seeds of these three additional inbred lines have been deposited under the Budapest Treaty in the American Type Culture Collection. One of these deposits has been designated *Brassica napus* W1W1 and has received Accession No. 75990, one of these deposits has been designated *Brassica napus* H4H4 and has received Accession No. 75991, and another of the deposits has been designated *Brassica napus* H5H5 and has received Accession No. 75992. When such genetic determinants are converted to the heterozygous state, they are suitable for use in the improved hybridization process of the present invention.

EXAMPLE III

Plants of *Brassica napus* ssp. *rapifera* were chosen as a source of a dominant genetic determinant for the sporophytic self-incompatibility required to carry out the improved hybridization process of the present invention. Cyclic inbreeding as described in connection with Example I was utilized to identify a rapeseed of a line that contains a requisite determinant for self-incompatibility. This is the same self-incompatibility allele as identified as 2 in the Ph.D. dissertations of the P. Banks and J. P. Parker of the University of Guelph identified earlier. This allele was introgressed into the Regent cultivar of *Brassica napus* in the homozygous state as described in connection with the final portion of Example II. Following multiplication, seeds of this inbred line that are homozygous dominant for the self-incompatibility determinant have been deposited under the Budapest Treaty in the American Type Culture Collection under the *Brassica napus* R2R2 designation, and have received Accession No. 75993. When such genetic determinant is converted to the heterozygous state, it is suitable for use in the improved hybridization process of the present invention.

EXAMPLE IV

Plants of *Brassica oleracea* ssp. *italica* were chosen as the source for dominant genetic determinants for the sporophytic self-incompatibility required to carry out the improved hybridization process of the present invention. Cyclic inbreeding as described in connection with Example I was utilized to identify rapeseeds of two different lines derived from *Brassica oleracea* ssp. *italica* containing different homozygous dominant determinants for sporophytic self-incompatibility. There determinants were introgressed into *Brassica napus* plants of the Topas cultivar in the homozygous state. These were the same self-incompatibility alleles as identified as s2 and s13 in "Non-linear Dominance Relationships Between s Alleles" by K. F. Thompson and J. P. Taylor, Heredity 21:345 to 361 (1966). Following multiplication, seeds of these two inbred lines were deposited under the Budapest Treaty in the American Type Culture Collection. Seeds designed *Brassica napus* s2s2 have received Assession No. 75994, and seeds designated *Brassica napus* s13s13 have received Assession No. 75995. When such genetic determinant is converted to the heterozygous state, it is suitable for use in the improved hybridization process of the present invention. When such genetic determinants are converted to the heterozygous state, they are suitable for use in the improved hybridization process of the present invention.

EXAMPLE V

*Brassica campestris* foundation or basic seeds for use in the improved hybridization process of the present invention that contain the dominant genetic determinants for sporophytic self-incompatibility present in *Brassica campestris* BB (Example I), *Brassica campestris* EE (Example I), *Brassica campestris* PP (Example II) and *Brassica campestris* bb (Example II) in the heterozygous state were formed during the mixed planting of seeds of different inbred lines of the same species that each carry a different allele for self-incompatibility. More specifically, the other inbred in each instance was of the same cultivar (i.e., the Tobin cultivar for *Brassica campestris* BB and *Brassica campestris* EE of Example I in one instance, and the Candle cultivar for *Brassica campestris* PP and *Brassica campestris* bb of Example II in another instance). Following the cross-pollinations while growing in isolated blocks the resulting seeds were harvested in bulk and each contained two different dominant self-incompatibility alleles in the heterozygous state at the same locus. The quantity of available seed of each cross was multiplied many times and was suitable for use in the production of $F_1$ hybrids in accordance with the improved hybridization process of the present invention as described hereafter.

EXAMPLE VI

In order to produce seeds capable of forming predetermined $F_1$ hybrids of *Brassica campestris* in a large quantity in accordance with the improved process of the present invention, a randomly mixed population of plants derived from the two heterozygotes of Example V were grown in a planting area in an isolated location so as to preclude unwanted pollination from another source. More specifically, one parent contained dominant alleles for sporophytic self-incompatibility derived from *Brassica campestris* BB and *Brassica campestris* EE in the heterozygous state at the same locus, and one parent and contained dominant alleles for sporophytic self-incompatibility derived from *Brassica campestris* PP and *Brassica campestris* bb in the heterozygous state at the same locus which corresponds to the self-incompatibility locus of the other parent. Following cross-pollination and seed set, the resulting seeds were harvested in bulk and were capable of forming a predetermined cultivar of $F_1$ hybrid *Brassica campestris*. When growing in the planting area all plants served (1) as seed parents which upon cross-pollination with pollen from other parent plants formed seeds capable for yielding $F_1$ hybrid plants of a predetermined variety, and (2) as pollen parents for the other parent plants.

EXAMPLE VII

*Brassica napus* foundation or basic seeds for use in the improved hybridization process of the present invention that contain the dominant genetic determinants for sporophytic self-incompatibility present in *Brassica napus* W1W1 (Example II), *Brassica napus* H4H4 (Example II), *Brassica napus* H5H5 (Example II), *Brassica napus* R2R2, (Example III), *Brassica napus* s2s2 (Example IV), and *Brassica napus* s13s13 (Example IV), in the heterozygous state were formed during the mixed planting at isolated locations of seeds of different inbred lines that each carry a different allele for self-incompatibility. More specifically, seeds of *Brassica napus* W1W1 and *Brassica napus* H5H5 were mixed planted, seeds of *Brassica napus* s2s2 and *Brassica napus* s13s13 were mixed planted, and seeds of *Brassica napus* R2R2 and *Brassica napus* H4H4 were mixed planted. Following cross-pollination while growing in isolated blocks, the resulting seeds in each instance were harvested in bulk. The seeds resulting from the crosses each contained two different dominant self-incompatibility alleles in the heterozygous state at a common locus. However, the common locus was different for the cross between *Brassica napus* s2s2 and *Brassica napus* s13s13 than for the other crosses, since the operative alleles for this cross were derived from *Brassica oleracea*, while the operative alleles in the other two crosses were derived from *Brassica campestris*. The quantity of available seed was multiplied many times and was suitable for use in the production of $F_1$ hybrids in accordance with the improved hybridization process of the present invention.

EXAMPLE VIII

In order to produce seeds capable of forming predetermined $F_1$ hybrids of *Brassica napus* in a large quantity, substantially randomly mixed populations of plants derived from various combinations of the heterozygotes of Example VII were grown in planting areas in isolated locations so as to preclude pollination from another source. More specifically, in one instance, a cross was made between a parent that was the product of *Brassica napus* W1W1 and *Brassica napus* H5H5, and a parent that was the product of *Brassica napus* R2R2 and *Brassica napus* H4H4. In this instance, each parent possessed two heterozygous dominant genetic determinants for sporophytic self-incompatibility at the same locus that were different between each parent. In another instance, a cross was made between a parent that was the product of *Brassica napus* W1W1 and *Brassica napus* H5H5, and a parent that was the product of *Brassica napus* s2s2 and *Brassica napus* s13s13. In this instance, each parent possessed two heterozygous dominant genetic determinants for sporophytic self-incompatibility that were located at a different loci in each parent, since in the first parent the genetic determinants were derived from *Brassica campestris*, and in the second parent the genetic determinants were derived from *Brassica oleracea*. All plants in each planting area served (1) as seed parents which upon cross-pollination with pollen from the other parent plants formed seeds capable of yielding $F_1$ hybrid plants of a predetermined variety, and (2) as pollen parents for the other parent plants. The resulting seeds formed in each planting area were harvested in bulk and were capable of forming a predetermined cultivar of $F_1$ hybrid plants.

Although the invention has been described with preferred embodiments, it is to be understood that variations and modifications may be resorted to as will be apparent to those skilled in the art. Such variations and modifications are to be considered within the purview and scope of the claims appended hereto.

We claim:

1. An improved process for producing seeds to make a predetermined $F_1$ hybrid comprising:
   (a) growing in a planting area a randomly mixed population of parent plants which exhibit sporophytic self-incompatibility that are incapable of undergoing self-fertilization wherein the inability to undergo self-fertilization is attributable in each parent to at least two heterozygous dominant genetic determinants for sporophytic self-incompatibility that are different in each parent wherein said plants present in said planting area are capable of serving (1) as seed parents which following cross-pollination with pollen from the other parent plants bear seeds capable of forming predetermined $F_1$ hybrid plants of a predetermined cultivar and (2) as pollen parents for the parent plants growing in said planting area,
   (b) cross-pollinating said plants growing in said planting area with pollen derived from the other parent plants growing in said planting area and forming seeds capable of producing a predetermined cultivar of $F_1$ hybrid on said plants growing in said planting area as a result of said cross-pollination, and
   (c) harvesting in bulk said seeds that are capable of forming a predetermined cultivar of $F_1$ hybrid plants that form on both parent plants of said planting area.

2. An improved process for producing seeds to make a predetermined $F_1$ hybrid according to claim 1 wherein said heterozygous dominant genetic determinants for sporophytic self-incompatibility are located at different loci within each of said parent plants.

3. An improved process for producing seeds to make a predetermined $F_1$ hybrid according to claim 1 wherein said heterozygous dominant genetic determinants for sporophytic self-incompatibility are located at the same locus or loci within each of said parent plants.

4. An improved process for producing seeds to make a predetermined $F_1$ hybrid according to claim 1 wherein said crop is an oilseed crop.

5. An improved process for producing seeds to make a predetermined $F_1$ hybrid according to claim 1 wherein said $F_1$ hybrid is *Brassica napus*.

6. An improved process for producing seeds to make a predetermined $F_1$ hybrid according to claim 1 wherein said $F_1$ hybrid is *Brassica campestris*.

7. An improved process for producing seeds to make a predetermined $F_1$ hybrid according to claim 5 wherein said different genetic determinants for said sporophytic self-incompatibility present in said parent plants are derived from *Brassica oleracea* or *Brassica campestris*.

8. An improved process for producing seeds to make a predetermined $F_1$ hybrid according to claim 5 wherein said different genetic determinants for said sporophytic self-incompatibility present in said parent plants are derived from *Brassica oleracea* and *Brassica campestris*.

9. An improved process for producing seeds to make a predetermined $F_1$ hybrid according to claim 1 wherein said mixed population of parent plants was produced following the simultaneous planting of each parent in said planting area of a seed blend that forms each of said parent plants.

10. An improved process for producing seeds to make a predetermined $F_1$ hybrid according to claim 1 wherein said mixed population of parent plants was produced following the planting in said planting area on different dates of each of the parent plants so as to accommodate differences in the flowering characteristics of the two parents.

11. An improved process for producing seeds to make a predetermined $F_1$ hybrid according to claim 1 wherein each of said parents was formed through the controlled crossing of plants which were homozygous dominant for said at least two genetic determinants for sporophytic self-incompatibility with plants that are lacking in said at least two dominant genetic determinants for sporophytic self-incompatibility followed by the selective harvesting of the resulting seeds, and wherein in at least one earlier generation progenitor plants which are homozygous dominant for said at least two genetic determinants for sporophytic self-incompatibility were maintained through self-pollination by the use of means to overcome said sporophytic self-incompatibility.

12. An improved process for producing seeds to make a predetermined $F_1$ hybrid according to claim 11 wherein said means to overcome said sporophytic self-incompatibility comprised exposure to an increased level of carbon dioxide at the flowering time and/or the exposure of stigmas to a dilute aqueous solution of sodium chloride.

13. An improved process for producing seeds to make a predetermined $F_1$ hybrid according to claim 1 wherein each of said parents is formed through the crossing of plants which were homozygous dominant for said at least two genetic determinants for sporophytic self-incompatibility with plants which are lacking in said at least two dominant genetic determinants for sporophytic self-incompatibility while growing as a randomly mixed population and the resulting seed formed thereon is harvested in bulk, and wherein in at least one earlier generation progenitor plants which are homozygous dominant for said at least two genetic determinants for sporophytic self-incompatibility are maintained through self-pollination by the use of means to overcome said sporophytic self-incompatibility.

* * * * *